United States Patent
Kishikawa et al.

(10) Patent No.: US 7,151,093 B2
(45) Date of Patent: Dec. 19, 2006

(54) USE OF SPHINGOSINE 1-PHOSPHATE AS ACTIVE INGREDIENT FOR THE TREATMENT OF PULMONARY FIBROSIS

(75) Inventors: Katsuya Kishikawa, Mishima-gun (JP); Shigeru Matsumoto, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 340 days.

(21) Appl. No.: 10/661,580

(22) Filed: Sep. 15, 2003

(65) Prior Publication Data

US 2004/0063667 A1 Apr. 1, 2004

Related U.S. Application Data

(63) Continuation of application No. 10/030,314, filed as application No. PCT/JP00/04583 on Jul. 10, 2000, now abandoned.

(30) Foreign Application Priority Data

Jul. 12, 1999 (JP) ................. 11-196892

(51) Int. Cl.
*A61K 31/66* (2006.01)
(52) U.S. Cl. .................... 514/114; 514/119
(58) Field of Classification Search ............. 514/114, 514/119
See application file for complete search history.

(56) References Cited

U.S. PATENT DOCUMENTS

| 4,791,105 A | 12/1988 | Yamatsa et al. |
| 5,260,288 A | 11/1993 | Igarashi et al. |
| 5,374,616 A | 12/1994 | Spiegel et al. |
| 5,556,843 A | 9/1996 | Romeo et al. |
| 5,583,160 A | 12/1996 | Igarashi et al. |
| 5,627,171 A | 5/1997 | Park et al. |
| 5,663,404 A | 9/1997 | Igarashi et al. |
| 5,712,262 A | 1/1998 | Spiegel |
| 5,877,167 A | 3/1999 | Igarashi et al. |
| 6,210,976 B1 | 4/2001 | Sabbadini |
| 6,423,508 B1 * | 7/2002 | Bergsma et al. ........... 435/69.1 |

FOREIGN PATENT DOCUMENTS

WO    WO 93/19760 A1    10/1993

OTHER PUBLICATIONS

"Medical Encylopeia:Idiopathic Pulmonary Fibrosis", Medline Plus, 2004.*
"Medical Encyclopedia: Chronic Renal Failure", Medline Plus, 2005.*
"Hepaptitis C", DrugDigest, 2005.*
"Attenuation of Bleomycin-Induced Pulmonary Fibrosis by a Catalytic Antioxidant Metalloporphyrin", Oury et al., Am. J. Respir. Cell Mol. Biol., vol. 25, pp. 164-169, 2001.*
"Attenuation of Bleomycin-Induced Lung Fibrosis in Rats by Mesna", El-Medany et al., European Journal of Pharmacology, 509, 2005, pp. 61-70.*
C. Gallois et al., Endothelin-1 Stimulates Sphingosine Kinase in Human Hepatic Stellate Cells. A Novel Role for Sphingosine-1-P as a Mediator of Growth Inhibition, Annals of the New York Academy of Sciences, (2000) vol. 905, pp. 311-314.
James R. Van Brocklyn, Dual Actions of Sphingosine-1-Phosphate: Extracellular Through the $G_1$ coupled Receptor Edg-1 and Intracellular to Regulate Proliferation and Survival, The Journal of Cell Biology, (1998) vol. 142, No. 1, pp. 229-240.
Ariarie Mallat et al., Growth Inhibitory Properties of Endothelin-1 in Activated Human Hepatic Stellate Cells: A Cyclic Adenosine Monophosphate-mediated Pathway, Journal of Clinical Investigations, (1996) vol. 98, No. 12, pp. 2770-2778.

* cited by examiner

*Primary Examiner*—Brian Kwon
(74) *Attorney, Agent, or Firm*—Sughrue Mion, PLLC

(57) ABSTRACT

An anti fibrotic agent, comprising a sphingosine 1-phosphate (S1P) receptor agonist or sphingosine 1-phosphate (S1P) as an active ingredient. Since an S1P receptor agonist, particularly S1P, has activity of inhibiting fibrosis in various organs, it is useful in preventing and/or treating diseases caused by fibrosis in organs, such as pulmonary fibrosis, interstitial pneumonia, chronic hepatitis, hepatic cirrhosis, chronic renal failure, renal glomerulosclerosis, etc.

1 Claim, No Drawings

USE OF SPHINGOSINE 1-PHOSPHATE AS ACTIVE INGREDIENT FOR THE TREATMENT OF PULMONARY FIBROSIS

This is a continuation of application Ser. No. 10/030,314 filed Jan. 10, 2002, now abandoned which is a 371 of PCT/JP00/04583 filed Jul. 10, 2000, the disclosures of which are incorporated herein by reference.

TECHNICAL FIELD

The present invention relates to an anti fibrotic agent comprising a sphingosine 1-phosphate receptor agonist as an active ingredient. Particularly, the present invention relates to an anti fibrotic agent, comprising, as an active ingredient, sphingosine 1-phosphate represented by the following formula:

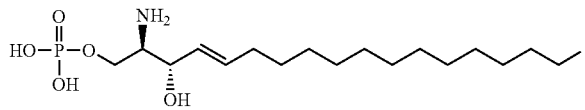

BACKGROUND OF THE INVENTION

Sphingolipid as one of the cell membrane-constituting lipid-soluble components contains two kinds, sphingomyelin and glycolipid. They are converted into ceramides enzymatically via sphingomyelinase and endoglycanase, and then metabolized into sphingosine by a ceramidase. Furthermore, the sphingosine is then converted into sphingosine 1-phosphate (hereinafter referred to as "S1P") by a sphingosine kinase.

Studies on such intracellular metabolism of sphingolipid have been carried out since 1960's, but until now, S1P has been recognized only as one of the intermediate metabolic products in the sphingolipid metabolism. However, S1P is focused because its physiological activities are being revealed recently.

For example, the followings are known as the activities possessed by S1P.
(1) Cell growth accelerating activity on Swiss 3T3 fibroblast by calcium mobilization (*J. Cell. Biol.*, 114, 155–167 (1991)).
(2) Control of cellular chemotactic activity of a cancer cell line (*Proc. Natl. Acad. Sci. USA*, 89, 9686–9690 (1992)).
(3) Inhibition of PDGF (platelet-derived growth factor)-dependent cellular mobilization of smooth muscle cells (*J. Cell. Biol.*, 130, 193–206 (1995)).
(4) Function as a second messenger. For example, S1P acts as an intracellular second messenger in a cell growth stimulation by PDGF etc. (*Nature*, 365, 557–560 (1993)) and it also acts as an intracellular second messenger in the intracellular calcium mobilization via a high affinity IgE receptor of a rat mast cell, RBL-2H3 cell (*Nature*, 380, 634–636 (1996)).
(5) Inhibition of apoptosis by ceramide etc. (*Nature*, 381, 800–803 (1996)). Opposite activity is suggested a possibility that it acts as a signal molecule of apoptosis induction of leukocyte (*FEBS Lett.*, 355, 267 (1995)), which may have a different mechanism.
(6) Since S1P has been reported to act as an extracellular moiety via a cell surface receptor, its role as an intercellular messenger is also focused. In addition, with the recent advance in the identification and cloning of S1P receptors, Edg-1 (endothelial cell differentiation gene-1), Edg-3, AGR16/H218 (Edg-5), Edg-6 and Edg-8 have been reported as specific S1P receptors (*Science*, 279, 1552–1555 (1998), *Biochem. J.*, 330, 605–609 (1998), *FEBS Lett.*, 417, 279–282 (1997), *Blood*, 95, 2624–2629 (2000), *J. Biol. Chem.*, 275, 14281–14286 (2000)).

The specification of WO 93/19760 (JP-T-8-500816) describes a method for using S1P in the inhibition of active chemotactic property of tumor cells, inhibition of invasion of tumor cells, inhibition of inflammation by the active property of neutrophils, inhibition of metastasis of malignant tumor cells etc.

The specification is provided that a method for inhibiting inflammation. However, it merely describes that since the inflammation steps are dependent on the mobilization of neutrophils, S1P which inhibits the mobilization is expected to be useful in inhibiting the inflammation steps.

The specification of U.S. Pat. No. 5,712,262 describes that S1P suppressed programmed cell death.

While various physiological activities of S1P are being revealed as described above, its activities regarding fibrosis are also studied. For example, as shown in the above item (1), it has been confirmed that S1P accelerates cell growth of Swiss 3T3 fibroblast and acts as an intracellular signal molecule which mobilizes calcium from its intracellular store, and it has been confirmed thereafter that sphingosine derivatives have activities similar to S1P (*J. Biol. Chem.*, 273(36), 23585–23589 (1998)). Thus, it has been reported that S1P and its related substances are concerned in the growth of fibroblast.

DISCLOSURE OF THE INVENTION

As a result of extensive studies on the physiological activities possessed by S1P, the present inventors have found unexpectedly that it has activity of suppressing fibrosis of organs and thereby accomplished the present invention. This is a result which cannot be expected at all in view of the prior art but confirmed for the first time by the inventors based on experiments.

In addition, it is known that S1P receptors are expressed in each organ. For example, it is known that S1P receptors Edg-1, Edg-3, Edg-5 and Edg-6 are expressed in the lungs, and S1P receptors Edg-1, Edg-3 and Edg-5 are expressed in the liver and kidney (*Genomics*, 53, 164–169 (1998), B. B. A., 1484, 107–116 (2000)).

Thus, based on these facts, it was also found that inhibition of fibrosis in various organs by S1P receptor agonists can be fully predicted.

The present invention relates to an anti fibrotic agent for various organs, comprising an S1P receptor agonist as an active ingredient. Particularly, the present invention relates to an anti fibrotic agent for various organs, comprising S1P as an active ingredient.

The S1P used in the present invention is a known substance (CAS registration number: 26993-30-6) and is commercially available.

Regarding the S1P receptor of the present invention, all of the receptors so far known (e.g., Edg-1, Edg-3, AGR16/H218 (Edg-5), Edg-6 and Edg-8) and which will be identified in the future are included.

As the S1P receptor agonist of the present invention, all of the S1P receptor agonist compounds so far known and compounds which will be found in the future are included.

INDUSTRIAL APPLICABILITY

It has been known that S1P is concerned in the growth of fibroblast. In general, it is considered that growth of fibroblast leads to the acceleration of fibrosis in organs. However, the inventors have found a fact that S1P inhibits fibrosis, which is a completely opposite result of the commonly known information.

Accordingly, since S1P has activity of inhibiting fibrosis in various organs, it is useful in preventing and/or treating pulmonary fibrosis, interstitial pneumonia, chronic hepatitis, hepatic cirrhosis, chronic renal failure, renal glomerulosclerosis and the like.

Also, based on the fact that S1P inhibits fibrosis, it can be fully predicted that an S1P receptor agonist will inhibit fibrosis in organs.

Accordingly, since the S1P receptor agonist has activity of inhibiting fibrosis in various organs, it is considered to be useful in preventing and/or treating pulmonary fibrosis, interstitial pneumonia, chronic hepatitis, hepatic cirrhosis, chronic renal failure, renal glomerulosclerosis and the like.

Toxicity

Since toxicity of the S1P used in the present invention is low, it can be judged that it is sufficiently safe in using it as a medicament.

Application for Pharmaceuticals

The S1P receptor agonist or S1P of the present invention may normally be administered systemically or topically, usually by oral or parenteral administration.

The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 0.1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compounds of the present invention may be administered in the form of, for example, solid forms for oral administration, liquid forms for oral administration, injections, liniments or suppositories for parenteral administration.

Solid forms for oral administration include compressed tablets, pills, capsules, dispersible powders, and granules etc. Capsules include hard capsules and soft capsules.

In such solid forms, one or more of the active compound(s) may be admixed with vehicles (such as lactose, mannitol, glucose, microcrystalline cellulose, starch, etc.), binders (such as hydroxypropyl cellulose, polyvinylpyrrolidone or magnesium metasilicate aluminate, etc.), disintegrants (such as cellulose calcium glycolate, etc.), lubricants (such as magnesium stearate, etc.), stabilizing agents, and solution adjuvants (such as glutamic acid or aspartic acid, etc.) and prepared according to methods well known in normal pharmaceutical practice. The solid forms may, if desired, be coated with coating agents (such as sugar, gelatin, hydroxypropyl cellulose or hydroxypropylmethyl cellulose phthalate, etc.), or be coated with two or more films. And further, coating may include containment within capsules of absorbable materials such as gelatin.

Liquid forms for oral administration include pharmaceutically acceptable solutions, suspensions and emulsions, syrups and elixirs, etc. In such forms, one or more of the active compound(s) may be dissolved, suspended or emulsified into diluent(s) commonly used in the art (such as purified water, ethanol or a mixture thereof, etc.). Besides such liquid forms may also comprise some additives, such as wetting agents, suspending agents, emulsifying agents, sweetening agents, flavoring agents, aroma, preservative or buffering agent, etc.

Injections for parenteral administration include sterile aqueous, suspensions, emulsions and solid forms which are dissolved or suspended into solvent(s) for injection immediately before use. In injections, one or more of the active compound(s) may be dissolved, suspended or emulsified into solvent(s). The solvents may include distilled water for injection, physiological salt solution, vegetable oil, propylene glycol, polyethylene glycol, alcohol, e.g. ethanol, or a mixture thereof, etc. Injections may comprise some additives, such as stabilizing agents, solution adjuvants (such as glutamic acid, aspartic acid or POLYSORBATE80 (registered trade mark), etc.), suspending agents, emulsifying agents, soothing agent, buffering agents, preservative, etc. They may be sterilized at a final step, or may be prepared and compensated according to sterile methods. They may also be manufactured in the form of sterile solid forms (such as freeze-dried products) which may be dissolved in sterile water or some other sterile diluent(s) for injection immediately before use.

Other forms for parenteral administration include liquids for external use, ointments and endermic liniments, inhalations, sprays, suppositories and pessaries for vaginal administration which comprise one or more of the active compound(s) and may be prepared by methods known per se.

Sprays may comprise additional substances other than diluents, such as stabilizing agents (such as sodium sulfate), isotonic buffers (such as sodium chloride, sodium citrate or citric acid). For preparation of such sprays, for example, the method described in the U.S. Pat. Nos. 2,868,691 or 3,095,355 may be used.

BEST MODE FOR CARRYING OUT THE INVENTION

The activity of S1P to inhibit fibrosis of organs was confirmed by the following test.

Test Method

Production of Bleomycin-induced Lung Injury Model Animal:

Using each of ICR male mice and under pentobarbital (60 mg/kg, i.v.) anesthesia, the cervical region was shaved and the skin was incised for about 4 mm from under the larynx region along the median line. Next, the muscle layer covering upper trachea was peeled off to expose the trachea. Using a micro-syringe, physiological saline or bleomycin hydrochloride (0.03 mg/animal, manufactured by Nippon Kayaku) was administered tracheally (50 µl/animal) from the tracheal smooth muscle region between cricoid cartilage. After the administration, the incised region was closed and antibiotics were administered into the thigh intramuscularly in order to prevent infection. S1P (10 mg/5 ml/kg, 0.5% aqueous solution of carboxymethylcellulose sodium (CM-C.Na)-physiological saline, manufactured by Matreya) was intraperitoneally administered once a day for 14 days after the bleomycin induction. Tests on the physiological saline group (normal group) and bleomycin-induced groups (control group and S1P-administered group) were each carried out using 10 animals. Fifteen days after the induction, each animal was sacrificed by exsanguination under pentobarbital (60 mg/kg, i.v.) anesthesia, and a lung (1 mg) tissue was excised.

Measurement of the lung fibrosis was carried out based on the lung tissue hydroxyproline content as shown below.

The excised lung parenchyma was cut into fine strips of about 2 to 3 mm, transferred into a heat-resistant screw test tube using distilled water (0.4 ml) and then freeze-dried. After overnight freeze-drying, 6 N hydrochloric acid (2.5 ml) was added thereto to carry out hydrolysis at 110° C. for 24 hours. After the hydrolysis, this sample was neutralized with 6 N sodium hydroxide aqueous solution (2.5 ml). Thereafter, this was centrifuged (1,000×g, 5 minutes) and the resulting supernatant (25 µl) was used in the determination of hydroxyproline.

The hydrolyzed supernatant (25 µl) was mixed with borate-alanine buffer (2.475 ml) separately prepared, and potassium chloride (solid) was added thereto until it was saturated. To the mixture, 0.2 M chloramine T (0.6 ml) was added, and incubated at room temperature for 40 minutes for oxidation, and the oxidation was terminated with 3.6 M sodium thiosulfate (2 ml). Toluene (3 ml) was added thereto, followed by sufficiently mixing and heating for 30 minutes in a boiling water bath. Next, the resulting mixture was cooled with tap water, followed by centrifugation (1,000×g, 5 minutes) to separate the toluene layer (1.5 ml). Ehrlich's reagent (0.6 ml) was added thereto to carry out the color development at room temperature for 30 to 40 minutes. The absorbance of each sample was immediately measured at 560 nm, and the amount of hydroxyproline in the sample was calculated from a calibration curve. The results are shown in Table 1.

TABLE 1

|  | Bleomycin-induced S1P administered group [S] | Bleomycin-induced S1P unadministered group [C] | Physiological saline-induced S1P unadministered group [B] |
|---|---|---|---|
| Hydroxyproline content (µg/lung) | 227.8 ± 17.5 | 318.6 ± 10.2 | 217.3 ± 9.3 |

The inhibition ratio was calculated by the following equation.

$$\text{Inhibition ratio} = [\{(C-B)-(S-B)\} \div (C-B)] \times 100 \ (\%)$$

S: Hydroxyproline content in bleomycin-induced+S1P-administered group

C: Hydroxyproline content in bleomycin-induced+0.5% CMC Na-physiological saline-administered group B: Hydroxyproline content in physiological saline-induced+0.5% CMC.Na-physiological saline-administered group As the above result, S1P suppressed bleomycin-induced the increase of hydroxyproline content by ca. 90%.

FORMULATION EXAMPLES

Formulation Example 1

The following components were mixed in the usual way and then subjected to tablet making to thereby obtain 100 tablets containing 50 mg of the active ingredient per tablet.

| Sphingosine 1-phosphate | 5.0 g |
| Carboxymethylcellulose calcium (disintegrator) | 0.2 g |
| Magnesium stearate (lubricant) | 0.1 g |
| Microcrystalline cellulose | 4.7 g |

Formulation Example 2

The following components were mixed in the usual way, and the solution was sterilized in the usual way, dispensed in 5 ml into ampuls and then freeze-dried in the usual way to thereby obtain 100 ampuls containing 20 mg of the active ingredient per ampul.

| Sphingosine 1-phosphate | 5.0 g |
| Mannitol | 20 g |
| Distilled water | 500 ml |

The invention claimed is:

1. A method for treating pulmonary fibrosis, said method comprising administering to a patient in need thereof an effective amount of an antifibrotic agent consisting of a sphingosine 1-phosphate as an active ingredient and a pharmaceutically acceptable carrier to treat pulmonary fibrosis.

* * * * *